United States Patent
Wolff et al.

(10) Patent No.: US 11,919,539 B2
(45) Date of Patent: Mar. 5, 2024

(54) PASSENGER HEALTH SCREENING AND MONITORING

(71) Applicant: Motional AD LLC, Boston, MA (US)

(72) Inventors: Eric Wolff, Boston, MA (US); Abhimanyu Singh, Singapore (SG); Linh Pham, Cambridge, MA (US)

(73) Assignee: Motional AD LLC, Boston, MA (US)

( * ) Notice: Subject to any disclaimer, the term of this patent is extended or adjusted under 35 U.S.C. 154(b) by 0 days.

(21) Appl. No.: 17/937,656

(22) Filed: Oct. 3, 2022

(65) Prior Publication Data

US 2023/0034871 A1    Feb. 2, 2023

Related U.S. Application Data

(63) Continuation of application No. 16/941,323, filed on Jul. 28, 2020, now Pat. No. 11,458,995.

(51) Int. Cl.
| | |
|---|---|
| *B60W 60/00* | (2020.01) |
| *A61B 5/00* | (2006.01) |
| *A61B 5/1171* | (2016.01) |
| *B60W 40/08* | (2012.01) |
| *G06V 40/16* | (2022.01) |

(52) U.S. Cl.
CPC ....... *B60W 60/0016* (2020.02); *A61B 5/1176* (2013.01); *A61B 5/6893* (2013.01); *A61B 5/747* (2013.01); *B60W 40/08* (2013.01); *G06V 40/168* (2022.01); *B60W 2540/221* (2020.02); *B60W 2556/10* (2020.02)

(58) Field of Classification Search
None
See application file for complete search history.

(56) References Cited

U.S. PATENT DOCUMENTS

| | | | |
|---|---|---|---|
| 9,988,055 | B1 | 6/2018 | O'Flaherty et al. |
| 11,458,995 | B2 | 10/2022 | Wolff et al. |
| 2016/0025603 | A1 | 1/2016 | Kindt et al. |
| 2018/0053411 | A1 | 2/2018 | Wieskamp et al. |
| 2018/0074494 | A1 | 3/2018 | Myers et al. |
| 2019/0091738 | A1 | 3/2019 | Chen et al. |
| 2019/0197325 | A1* | 6/2019 | Reiley .............. G08B 13/19602 |

(Continued)

FOREIGN PATENT DOCUMENTS

| | | |
|---|---|---|
| EP | 3459807 | 3/2019 |
| JP | H11-120494 | 4/1999 |

(Continued)

OTHER PUBLICATIONS

[No Author Listed], "SAE International: Surface Vehicle Recommended Practice Standard J3016: Taxonomy and Definitions for Terms Related to On-Road Motor Vehicle Automated Driving Systems, " Sep. 30, 2020, 30 pages.

*Primary Examiner* — James J Lee
*Assistant Examiner* — Andrew Sang Kim
(74) *Attorney, Agent, or Firm* — Fish & Richardson P.C.

(57) ABSTRACT

Among other things, techniques are described for screening and monitoring the health of a vehicle user including receiving sensor data produced by a sensor at the vehicle, processing the sensor data to determine at least one health condition of the user of the vehicle, and in response to determining the at least one health condition, executing a vehicle function selected from a plurality of vehicle functions based on the at least one health condition.

17 Claims, 11 Drawing Sheets

(56) References Cited

U.S. PATENT DOCUMENTS

| | | | |
|---|---|---|---|
| 2019/0232974 A1 | 8/2019 | Reiley et al. | |
| 2019/0258253 A1 | 8/2019 | Tremblay | |
| 2019/0359056 A1* | 11/2019 | Wilson | G08B 21/06 |
| 2019/0391581 A1* | 12/2019 | Vardaro | A61B 5/02055 |
| 2020/0061223 A1 | 2/2020 | Hallack | |
| 2020/0104770 A1* | 4/2020 | Aich | G01C 21/3423 |
| 2020/0114929 A1 | 4/2020 | Wan et al. | |
| 2020/0130703 A1 | 4/2020 | Pendelton et al. | |
| 2020/0202148 A1 | 6/2020 | Wright et al. | |
| 2020/0353934 A1* | 11/2020 | Vulcu | A61B 5/165 |
| 2021/0031788 A1* | 2/2021 | Tatsumoto | B60R 1/00 |
| 2021/0307621 A1 | 10/2021 | Svenson et al. | |
| 2022/0032956 A1 | 2/2022 | Wolff et al. | |

FOREIGN PATENT DOCUMENTS

| | | |
|---|---|---|
| JP | 2000-099867 | 4/2000 |
| KR | 10-1706142 B1 | 2/2017 |
| KR | 2019-0106843 | 9/2019 |
| KR | 10-2020-0079277 | 7/2020 |
| WO | WO 2008/111091 | 9/2008 |
| WO | WO 2016/197068 | 12/2016 |
| WO | WO 2021/159630 | 8/2021 |

* cited by examiner

PASSENGER HEALTH SCREENING AND MONITORING

CROSS-REFERENCE TO RELATED APPLICATIONS

This application is a continuation of U.S. application Ser. No. 16/941,323, filed Jul. 28, 2020 (now allowed), which is incorporated herein by reference in its entirety.

FIELD OF THE INVENTION

This description relates to screening and monitoring the health of vehicle users.

BACKGROUND

A vehicle, such as an autonomous vehicle, can include sensors that produce data regarding objects or persons within or proximate to the vehicle.

DETAILED DESCRIPTION

Figure 1:
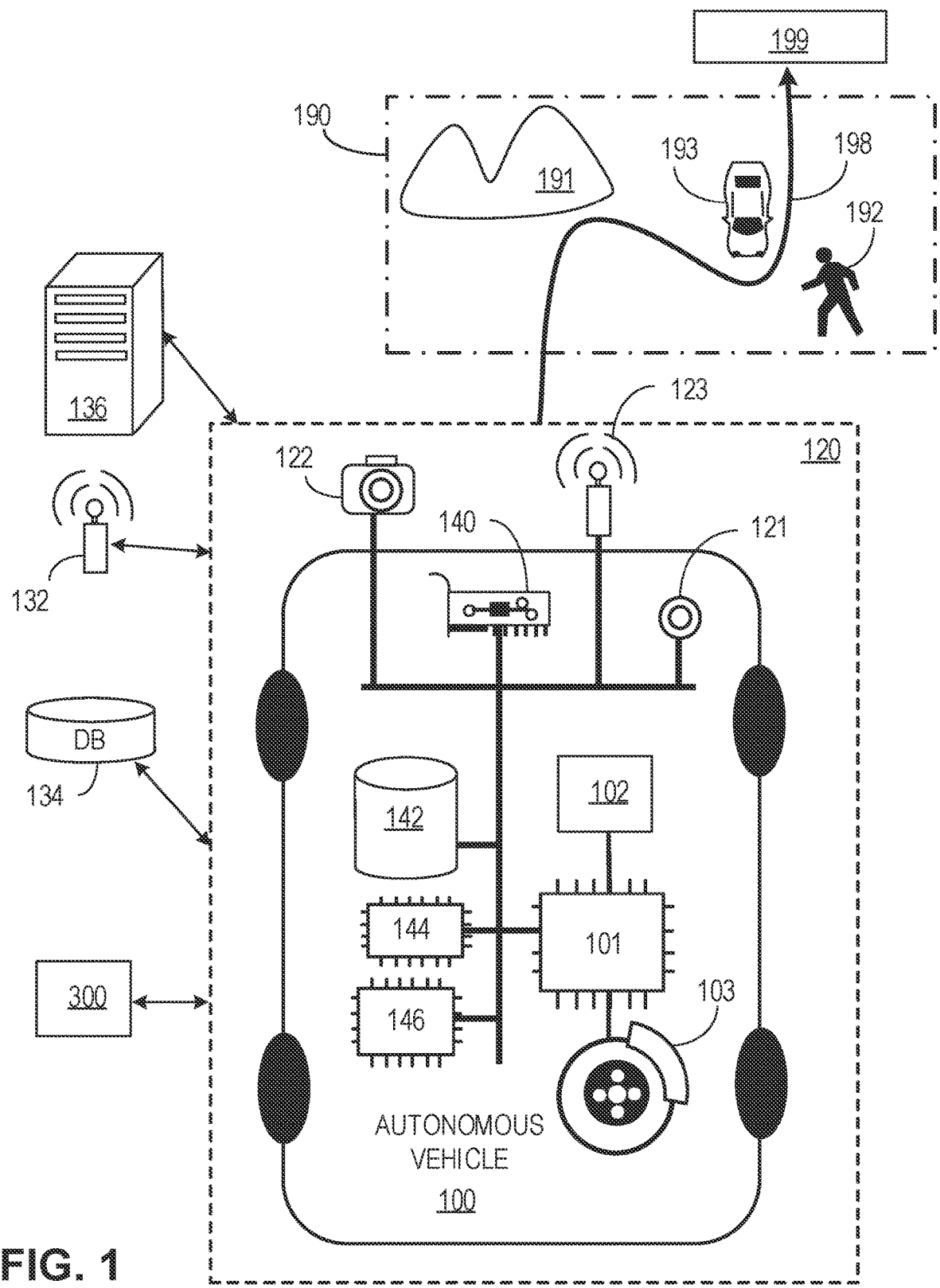
FIG. 1 shows an example of an autonomous vehicle having autonomous capability.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

In the drawings, specific arrangements or orderings of schematic elements, such as those representing devices, modules, instruction blocks and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood by those skilled in the art that such element represents one or multiple signal paths (e.g., a bus), as may be needed, to affect the communication.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

Several features are described hereafter that can each be used independently of one another or with any combination of other features. However, any individual feature may not address any of the problems discussed above or might only address one of the problems discussed above. Some of the problems discussed above might not be fully addressed by any of the features described herein. Although headings are provided, information related to a particular heading, but not found in the section having that heading, may also be found elsewhere in this description. Embodiments are described herein according to the following outline:

1. General Overview
2. System Overview
3. Autonomous Vehicle Architecture
4. Autonomous Vehicle Inputs
5. Autonomous Vehicle Planning
6. Autonomous Vehicle Control
7. Passenger Health Monitoring and Screening General Overview A vehicle (such as an autonomous vehicle) can process data from one or more sensors to monitor for one or more health conditions of a user, e.g., as the user approaches or travels within the vehicle. For example, audio data from an audio sensor (e.g., microphone) at the vehicle is processed to detect and characterize a cough by the user which can then be used to diagnose the user with a particular health condition. As another example, data from a temperature sensor is processed to determine the body temperature of the user and infer whether the user shows signs of a fever or other illness. In response to determining that the user may have a particular health condition, the vehicle can execute one or more vehicle functions based on the health condition, such as alerting the user of the health condition, rerouting the vehicle to the nearest emergency services, or applying a disinfectant within the vehicle when the user exits the vehicle, among others.

Some of the advantages of these techniques include using vehicle sensors to monitor the health of vehicle users or potential users. This health information can then be used by the vehicle to adjust vehicle functions in order to accommodate the user's health condition, prevent the user's health from worsening, or transport the user to a hospital or other emergency service for care, if necessary. The vehicle can also use the health information to inform the user of a potential health condition that they may not be aware of. In some examples, the vehicle uses the health information to carry out appropriate cleaning procedures after the user has exited the vehicle to prevent spread to subsequent users.

System Overview

FIG. 1 shows an example of an autonomous vehicle 100 having autonomous capability.

As used herein, the term "autonomous capability" refers to a function, feature, or facility that enables a vehicle to be partially or fully operated without real-time human intervention, including without limitation fully autonomous vehicles, highly autonomous vehicles, and conditionally autonomous vehicles.

As used herein, an autonomous vehicle (AV) is a vehicle that possesses autonomous capability.

As used herein, "vehicle" includes means of transportation of goods or people. For example, cars, buses, trains, airplanes, drones, trucks, boats, ships, submersibles, dirigibles, etc. A driverless car is an example of a vehicle.

As used herein, "trajectory" refers to a path or route to navigate an AV from a first spatiotemporal location to second spatiotemporal location. In an embodiment, the first spatiotemporal location is referred to as the initial or starting location and the second spatiotemporal location is referred to as the destination, final location, goal, goal position, or goal location. In some examples, a trajectory is made up of one or more segments (e.g., sections of road) and each segment is made up of one or more blocks (e.g., portions of a lane or intersection). In an embodiment, the spatiotemporal locations correspond to real world locations. For example, the spatiotemporal locations are pick up or drop-off locations to pick up or drop-off persons or goods.

As used herein, "sensor(s)" includes one or more hardware components that detect information about the environment surrounding the sensor. Some of the hardware components can include sensing components (e.g., image sensors, biometric sensors), transmitting and/or receiving components (e.g., laser or radio frequency wave transmitters and receivers), electronic components such as analog-to-digital converters, a data storage device (such as a RAM and/or a nonvolatile storage), software or firmware components and data processing components such as an ASIC (application-specific integrated circuit), a microprocessor and/or a microcontroller.

As used herein, a "scene description" is a data structure (e.g., list) or data stream that includes one or more classified or labeled objects detected by one or more sensors on the AV vehicle or provided by a source external to the AV.

As used herein, a "road" is a physical area that can be traversed by a vehicle, and may correspond to a named thoroughfare (e.g., city street, interstate freeway, etc.) or may correspond to an unnamed thoroughfare (e.g., a driveway in a house or office building, a section of a parking lot, a section of a vacant lot, a dirt path in a rural area, etc.). Because some vehicles (e.g., 4-wheel-drive pickup trucks, sport utility vehicles, etc.) are capable of traversing a variety of physical areas not specifically adapted for vehicle travel, a "road" may be a physical area not formally defined as a thoroughfare by any municipality or other governmental or administrative body.

As used herein, a "lane" is a portion of a road that can be traversed by a vehicle. A lane is sometimes identified based on lane markings. For example, a lane may correspond to most or all of the space between lane markings, or may correspond to only some (e.g., less than 50%) of the space between lane markings. For example, a road having lane markings spaced far apart might accommodate two or more vehicles between the markings, such that one vehicle can pass the other without traversing the lane markings, and thus could be interpreted as having a lane narrower than the space between the lane markings, or having two lanes between the lane markings. A lane could also be interpreted in the absence of lane markings. For example, a lane may be defined based on physical features of an environment, e.g., rocks and trees along a thoroughfare in a rural area or, e.g., natural obstructions to be avoided in an undeveloped area. A lane could also be interpreted independent of lane markings or physical features. For example, a lane could be interpreted based on an arbitrary path free of obstructions in an area that otherwise lacks features that would be interpreted as lane boundaries. In an example scenario, an AV could interpret a lane through an obstruction-free portion of a field or empty lot. In another example scenario, an AV could interpret a lane through a wide (e.g., wide enough for two or more lanes) road that does not have lane markings. In this scenario, the AV could communicate information about the lane to other AVs so that the other AVs can use the same lane information to coordinate path planning among themselves.

The term "over-the-air (OTA) client" includes any AV, or any electronic device (e.g., computer, controller, IoT device, electronic control unit (ECU)) that is embedded in, coupled to, or in communication with an AV.

The term "over-the-air (OTA) update" means any update, change, deletion or addition to software, firmware, data or configuration settings, or any combination thereof, that is delivered to an OTA client using proprietary and/or standardized wireless communications technology, including but not limited to: cellular mobile communications (e.g., 2G, 3G, 4G, 5G), radio wireless area networks (e.g., WiFi) and/or satellite Internet.

The term "edge node" means one or more edge devices coupled to a network that provide a portal for communication with AVs and can communicate with other edge nodes and a cloud based computing platform, for scheduling and delivering OTA updates to OTA clients.

The term "edge device" means a device that implements an edge node and provides a physical wireless access point (AP) into enterprise or service provider (e.g., VERIZON, AT&T) core networks. Examples of edge devices include but are not limited to: computers, controllers, transmitters, routers, routing switches, integrated access devices (IADs), multiplexers, metropolitan area network (MAN) and wide area network (WAN) access devices.

"One or more" includes a function being performed by one element, a function being performed by more than one element, e.g., in a distributed fashion, several functions being performed by one element, several functions being performed by several elements, or any combination of the above.

It will also be understood that, although the terms first, second, etc. are, in some instances, used herein to describe various elements, these elements should not be limited by these terms. These terms are only used to distinguish one element from another. For example, a first contact could be termed a second contact, and, similarly, a second contact could be termed a first contact, without departing from the scope of the various described embodiments. The first contact and the second contact are both contacts, but they are not the same contact.

The terminology used in the description of the various described embodiments herein is for the purpose of describing particular embodiments only and is not intended to be limiting. As used in the description of the various described embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this description, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

As used herein, an AV system refers to the AV along with the array of hardware, software, stored data, and data generated in real-time that supports the operation of the AV. In an embodiment, the AV system is incorporated within the AV. In an embodiment, the AV system is spread across several locations. For example, some of the software of the AV system is implemented on a cloud computing environment similar to cloud computing environment 300 described below with respect to FIG. 3.

In general, this document describes technologies applicable to any vehicles that have one or more autonomous capabilities including fully autonomous vehicles, highly autonomous vehicles, and conditionally autonomous vehicles, such as so-called Level 5, Level 4 and Level 3 vehicles, respectively (see SAE International's standard J3016: Taxonomy and Definitions for Terms Related to On-Road Motor Vehicle Automated Driving Systems, which is incorporated by reference in its entirety, for more details on the classification of levels of autonomy in vehicles). The technologies described in this document are also applicable to partially autonomous vehicles and driver assisted vehicles, such as so-called Level 2 and Level 1 vehicles (see SAE International's standard J3016: Taxonomy and Definitions for Terms Related to On-Road Motor Vehicle Automated Driving Systems). In an embodiment, one or more of the Level 1, 2, 3, 4 and 5 vehicle systems may automate certain vehicle operations (e.g., steering, braking, and using maps) under certain operating conditions based on processing of sensor inputs. The technologies described in this document can benefit vehicles in any levels, ranging from fully autonomous vehicles to human-operated vehicles.

Autonomous vehicles have advantages over vehicles that require a human driver. One advantage is safety. For example, in 2016, the United States experienced 6 million automobile accidents, 2.4 million injuries, 40,000 fatalities, and 13 million vehicles in crashes, estimated at a societal cost of $910+ billion. U.S. traffic fatalities per 100 million miles traveled have been reduced from about six to about one from 1965 to 2015, in part due to additional safety measures deployed in vehicles. For example, an additional half second of warning that a crash is about to occur is believed to mitigate 60% of front-to-rear crashes. However, passive safety features (e.g., seat belts, airbags) have likely reached their limit in improving this number. Thus, active safety measures, such as automated control of a vehicle, are the likely next step in improving these statistics. Because human drivers are believed to be responsible for a critical pre-crash event in 95% of crashes, automated driving systems are likely to achieve better safety outcomes, e.g., by reliably recognizing and avoiding critical situations better than humans; making better decisions, obeying traffic laws, and predicting future events better than humans; and reliably controlling a vehicle better than a human.

Referring to FIG. 1, an AV system 120 operates the AV 100 along a trajectory 198 through an environment 190 to a destination 199 (sometimes referred to as a final location) while avoiding objects (e.g., natural obstructions 191, vehicles 193, pedestrians 192, cyclists, and other obstacles) and obeying rules of the road (e.g., rules of operation or driving preferences).

In an embodiment, the AV system 120 includes devices 101 that are instrumented to receive and act on operational commands from the computer processors 146. We use the term "operational command" to mean an executable instruction (or set of instructions) that causes a vehicle to perform an action (e.g., a driving manuever). Operational commands can, without limitation, including instructions for a vehicle to start moving forward, stop moving forward, start moving backward, stop moving backward, accelerate, decelerate, perform a left turn, and perform a right turn. In an embodiment, computing processors 146 are similar to the processor 304 described below in reference to FIG. 3. Examples of devices 101 include a steering control 102, brakes 103, gears, accelerator pedal or other acceleration control mechanisms, windshield wipers, side-door locks, window controls, and turn-indicators.

In an embodiment, the AV system 120 includes sensors 121 for measuring or inferring properties of state or condition of the AV 100, such as the AV's position, linear and angular velocity and acceleration, and heading (e.g., an orientation of the leading end of AV 100). Example of sensors 121 are GPS, inertial measurement units (IMU) that measure both vehicle linear accelerations and angular rates, wheel speed sensors for measuring or estimating wheel slip ratios, wheel brake pressure or braking torque sensors, engine torque or wheel torque sensors, and steering angle and angular rate sensors.

In an embodiment, the sensors 121 also include sensors for sensing or measuring properties of the AV's environment. For example, monocular or stereo video cameras 122 in the visible light, infrared or thermal (or both) spectra, LiDAR 123, RADAR, ultrasonic sensors, time-of-flight (TOF) depth sensors, speed sensors, temperature sensors, humidity sensors, and precipitation sensors.

In an embodiment, the AV system 120 includes a data storage unit 142 and memory 144 for storing machine instructions associated with computer processors 146 or data collected by sensors 121. In an embodiment, the data storage unit 142 is similar to the ROM 308 or storage device 310 described below in relation to FIG. 3. In an embodiment, memory 144 is similar to the main memory 306 described below. In an embodiment, the data storage unit 142 and memory 144 store historical, real-time, and/or predictive information about the environment 190. In an embodiment, the stored information includes maps, driving performance, traffic congestion updates or weather conditions. In an embodiment, data relating to the environment 190 is transmitted to the AV 100 via a communications channel from a remotely located database 134.

In an embodiment, the AV system 120 includes communications devices 140 for communicating measured or inferred properties of other vehicles' states and conditions, such as positions, linear and angular velocities, linear and angular accelerations, and linear and angular headings to the AV 100. These devices include Vehicle-to-Vehicle (V2V) and Vehicle-to-Infrastructure (V2I) communication devices and devices for wireless communications over point-to-point or ad hoc networks or both. In an embodiment, the communications devices 140 communicate across the electromagnetic spectrum (including radio and optical communications) or other media (e.g., air and acoustic media). A combination of Vehicle-to-Vehicle (V2V) Vehicle-to-Infrastructure (V2I) communication (and, in some embodiments, one or more other types of communication) is sometimes referred to as Vehicle-to-Everything (V2X) communication. V2X communication typically conforms to one or more communications standards for communication with, between, and among autonomous vehicles.

In an embodiment, the communication devices 140 include communication interfaces. For example, wired, wireless, WiMAX, Wi-Fi, Bluetooth, satellite, cellular, optical, near field, infrared, or radio interfaces. The communication interfaces transmit data from a remotely located database 134 to AV system 120. In an embodiment, the remotely located database 134 is embedded in a cloud computing environment 200 as described in FIG. 2. The communication interfaces 140 transmit data collected from sensors 121 or other data related to the operation of AV 100 to the remotely located database 134. In an embodiment, communication interfaces 140 transmit information that relates to teleoperations to the AV 100. In some embodiments, the AV 100 communicates with other remote (e.g., "cloud") servers 136.

In an embodiment, the remotely located database 134 also stores and transmits digital data (e.g., storing data such as road and street locations). Such data is stored on the memory 144 on the AV 100, or transmitted to the AV 100 via a communications channel from the remotely located database 134.

In an embodiment, the remotely located database 134 stores and transmits historical information about driving properties (e.g., speed and acceleration profiles) of vehicles that have previously traveled along trajectory 198 at similar times of day. In one implementation, such data may be stored on the memory 144 on the AV 100, or transmitted to the AV 100 via a communications channel from the remotely located database 134.

Computing devices 146 located on the AV 100 algorithmically generate control actions based on both real-time sensor data and prior information, allowing the AV system 120 to execute its autonomous driving capabilities.

In an embodiment, the AV system 120 includes computer peripherals 132 coupled to computing devices 146 for providing information and alerts to, and receiving input from, a user (e.g., an occupant or a remote user) of the AV 100. In an embodiment, peripherals 132 are similar to the display 312, input device 314, and cursor controller 316 discussed below in reference to FIG. 3. The coupling is wireless or wired. Any two or more of the interface devices may be integrated into a single device.

In an embodiment, the AV system 120 receives and enforces a privacy level of a passenger, e.g., specified by the passenger or stored in a profile associated with the passenger. The privacy level of the passenger determines how particular information associated with the passenger (e.g., passenger comfort data, biometric data, etc.) is permitted to be used, stored in the passenger profile, and/or stored on the cloud server 136 and associated with the passenger profile. In an embodiment, the privacy level specifies particular information associated with a passenger that is deleted once the ride is completed. In an embodiment, the privacy level specifies particular information associated with a passenger and identifies one or more entities that are authorized to access the information. Examples of specified entities that are authorized to access information can include other AVs, third party AV systems, or any entity that could potentially access the information.

A privacy level of a passenger can be specified at one or more levels of granularity. In an embodiment, a privacy level identifies specific information to be stored or shared. In an embodiment, the privacy level applies to all the information associated with the passenger such that the passenger can specify that none of her personal information is stored or shared. Specification of the entities that are permitted to access particular information can also be specified at various levels of granularity. Various sets of entities that are permitted to access particular information can include, for example, other AVs, cloud servers 136, specific third party AV systems, etc.

In an embodiment, the AV system 120 or the cloud server 136 determines if certain information associated with a passenger can be accessed by the AV 100 or another entity. For example, a third-party AV system that attempts to access passenger input related to a particular spatiotemporal location must obtain authorization, e.g., from the AV system 120 or the cloud server 136, to access the information associated with the passenger. For example, the AV system 120 uses the passenger's specified privacy level to determine whether the passenger input related to the spatiotemporal location can be presented to the third-party AV system, the AV 100, or to another AV. This enables the passenger's privacy level to specify which other entities are allowed to receive data about the passenger's actions or other data associated with the passenger.

Figure 2:
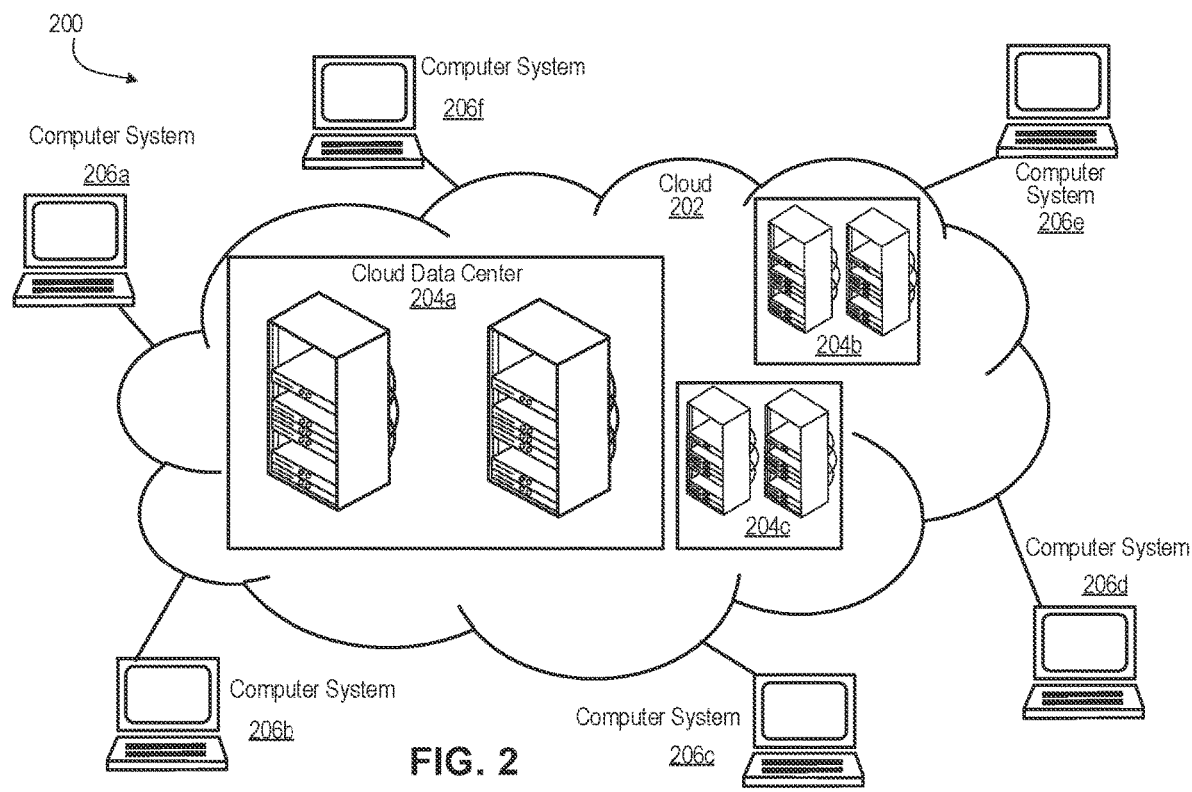
FIG. 2 shows an example "cloud" computing environment.

FIG. 2 illustrates an example "cloud" computing environment. Cloud computing is a model of service delivery for enabling convenient, on-demand network access to a shared pool of configurable computing resources (e.g. networks, network bandwidth, servers, processing, memory, storage, applications, virtual machines, and services). In typical cloud computing systems, one or more large cloud data centers house the machines used to deliver the services provided by the cloud. Referring now to FIG. 2, the cloud computing environment 200 includes cloud data centers 204a, 204b, and 204c that are interconnected through the cloud 202. Data centers 204a, 204b, and 204c provide cloud computing services to computer systems 206a, 206b, 206c, 206d, 206e, and 206f connected to cloud 202.

The cloud computing environment 200 includes one or more cloud data centers. In general, a cloud data center, for example the cloud data center 204a shown in FIG. 2, refers to the physical arrangement of servers that make up a cloud, for example the cloud 202 shown in FIG. 2, or a particular portion of a cloud. For example, servers are physically arranged in the cloud datacenter into rooms, groups, rows, and racks. A cloud datacenter has one or more zones, which include one or more rooms of servers. Each room has one or more rows of servers, and each row includes one or more racks. Each rack includes one or more individual server nodes. In some implementation, servers in zones, rooms, racks, and/or rows are arranged into groups based on physical infrastructure requirements of the datacenter facility, which include power, energy, thermal, heat, and/or other requirements. In an embodiment, the server nodes are similar to the computer system described in FIG. 3. The data center 204a has many computing systems distributed through many racks.

The cloud 202 includes cloud data centers 204a, 204b, and 204c along with the network and networking resources (for example, networking equipment, nodes, routers, switches, and networking cables) that interconnect the cloud data centers 204a, 204b, and 204c and help facilitate the computing systems' 206a-f access to cloud computing services. In an embodiment, the network represents any combination of one or more local networks, wide area networks, or internetworks coupled using wired or wireless links deployed using terrestrial or satellite connections. Data exchanged over the network, is transferred using any number of network layer protocols, such as Internet Protocol (IP), Multiprotocol Label Switching (MPLS), Asynchronous Transfer Mode (ATM), Frame Relay, etc. Furthermore, in embodiments where the network represents a combination of multiple sub-networks, different network layer protocols are used at each of the underlying sub-networks. In some embodiments, the network represents one or more interconnected internetworks, such as the public Internet.

The computing systems 206a-f or cloud computing services consumers are connected to the cloud 202 through network links and network adapters. In an embodiment, the computing systems 206a-f are implemented as various computing devices, for example servers, desktops, laptops, tablet, smartphones, Internet of Things (IoT) devices, autonomous vehicles (including, cars, drones, shuttles, trains, buses, etc.) and consumer electronics. In an embodiment, the computing systems 206a-f are implemented in or as a part of other systems.

Figure 3:
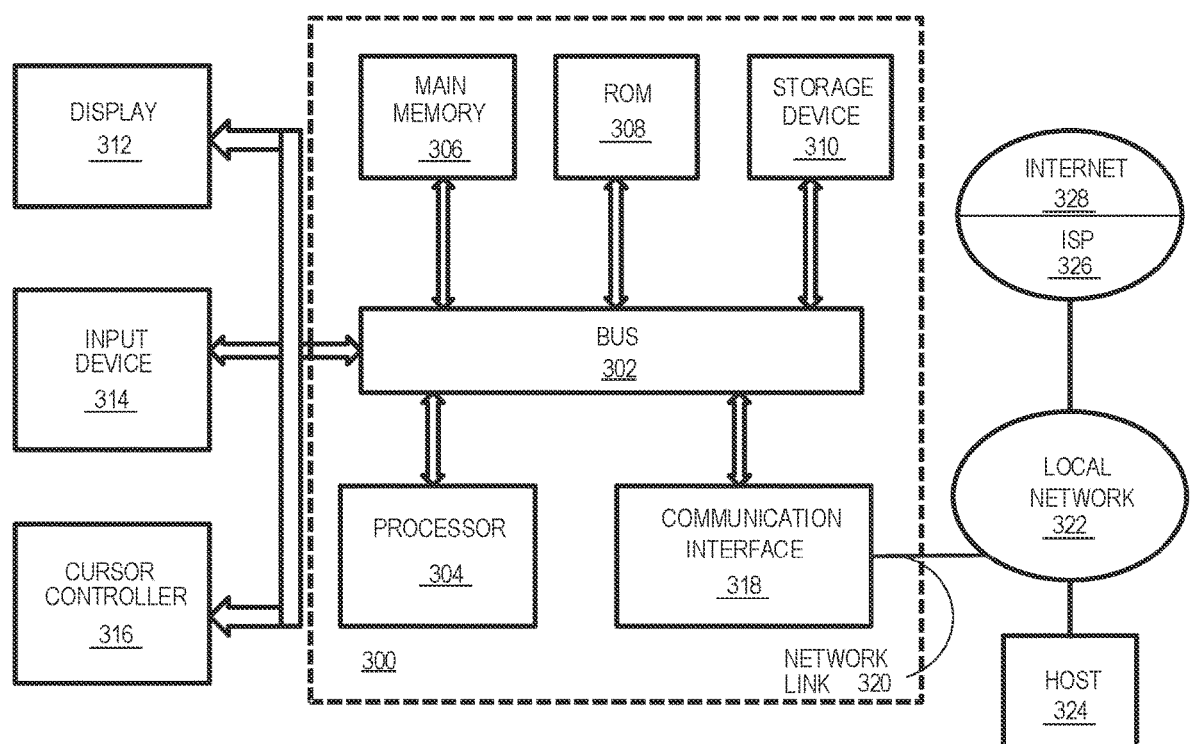
FIG. 3 shows an example computer system.

FIG. 3 illustrates a computer system 300. In an implementation, the computer system 300 is a special purpose computing device. The special-purpose computing device is hard-wired to perform the techniques or includes digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. In various embodiments, the special-purpose computing devices are desktop computer systems, portable computer systems, handheld devices, network devices or any other device that incorporates hard-wired and/or program logic to implement the techniques.

In an embodiment, the computer system 300 includes a bus 302 or other communication mechanism for communicating information, and a hardware processor 304 coupled with a bus 302 for processing information. The hardware processor 304 is, for example, a general-purpose microprocessor. The computer system 300 also includes a main memory 306, such as a random-access memory (RAM) or other dynamic storage device, coupled to the bus 302 for storing information and instructions to be executed by processor 304. In one implementation, the main memory 306 is used for storing temporary variables or other intermediate information during execution of instructions to be executed by the processor 304. Such instructions, when stored in non-transitory storage media accessible to the processor 304, render the computer system 300 into a special-purpose machine that is customized to perform the operations specified in the instructions.

In an embodiment, the computer system 300 further includes a read only memory (ROM) 308 or other static storage device coupled to the bus 302 for storing static information and instructions for the processor 304. A storage device 310, such as a magnetic disk, optical disk, solid-state drive, or three-dimensional cross point memory is provided and coupled to the bus 302 for storing information and instructions.

In an embodiment, the computer system 300 is coupled via the bus 302 to a display 312, such as a cathode ray tube (CRT), a liquid crystal display (LCD), plasma display, light emitting diode (LED) display, or an organic light emitting diode (OLED) display for displaying information to a computer user. An input device 314, including alphanumeric and other keys, is coupled to bus 302 for communicating information and command selections to the processor 304. Another type of user input device is a cursor controller 316, such as a mouse, a trackball, a touch-enabled display, or cursor direction keys for communicating direction information and command selections to the processor 304 and for controlling cursor movement on the display 312. This input device typically has two degrees of freedom in two axes, a first axis (e.g., x-axis) and a second axis (e.g., y-axis), that allows the device to specify positions in a plane.

According to one embodiment, the techniques herein are performed by the computer system 300 in response to the processor 304 executing one or more sequences of one or more instructions contained in the main memory 306. Such instructions are read into the main memory 306 from another storage medium, such as the storage device 310. Execution of the sequences of instructions contained in the main memory 306 causes the processor 304 to perform the process steps described herein. In alternative embodiments, hard-wired circuitry is used in place of or in combination with software instructions.

The term "storage media" as used herein refers to any non-transitory media that store data and/or instructions that cause a machine to operate in a specific fashion. Such storage media includes non-volatile media and/or volatile media. Non-volatile media includes, for example, optical disks, magnetic disks, solid-state drives, or three-dimensional cross point memory, such as the storage device 310. Volatile media includes dynamic memory, such as the main memory 306. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NV-RAM, or any other memory chip or cartridge.

Storage media is distinct from but may be used in conjunction with transmission media. Transmission media participates in transferring information between storage media. For example, transmission media includes coaxial cables, copper wire and fiber optics, including the wires that comprise the bus 302. Transmission media can also take the form of acoustic or light waves, such as those generated during radio-wave and infrared data communications.

In an embodiment, various forms of media are involved in carrying one or more sequences of one or more instructions to the processor 304 for execution. For example, the instructions are initially carried on a magnetic disk or solid-state drive of a remote computer. The remote computer loads the instructions into its dynamic memory and send the instructions over a telephone line using a modem. A modem local to the computer system 300 receives the data on the telephone line and use an infrared transmitter to convert the data to an infrared signal. An infrared detector receives the data carried in the infrared signal and appropriate circuitry places the data on the bus 302. The bus 302 carries the data to the main memory 306, from which processor 304 retrieves and executes the instructions. The instructions received by the main memory 306 may optionally be stored on the storage device 310 either before or after execution by processor 304.

The computer system 300 also includes a communication interface 318 coupled to the bus 302. The communication interface 318 provides a two-way data communication coupling to a network link 320 that is connected to a local network 322. For example, the communication interface 318 is an integrated service digital network (ISDN) card, cable modem, satellite modem, or a modem to provide a data communication connection to a corresponding type of telephone line. As another example, the communication interface 318 is a local area network (LAN) card to provide a data communication connection to a compatible LAN. In some implementations, wireless links are also implemented. In any such implementation, the communication interface 318 sends and receives electrical, electromagnetic, or optical signals that carry digital data streams representing various types of information.

The network link 320 typically provides data communication through one or more networks to other data devices. For example, the network link 320 provides a connection through the local network 322 to a host computer 324 or to a cloud data center or equipment operated by an Internet Service Provider (ISP) 326. The ISP 326 in turn provides data communication services through the world-wide packet data communication network now commonly referred to as the "Internet" 328. The local network 322 and Internet 328 both use electrical, electromagnetic or optical signals that carry digital data streams. The signals through the various networks and the signals on the network link 320 and through the communication interface 318, which carry the digital data to and from the computer system 300, are example forms of transmission media. In an embodiment, the network 320 contains the cloud 202 or a part of the cloud 202 described above.

The computer system 300 sends messages and receives data, including program code, through the network(s), the network link 320, and the communication interface 318. In an embodiment, the computer system 300 receives code for processing. The received code is executed by the processor 304 as it is received, and/or stored in storage device 310, or other non-volatile storage for later execution.

Autonomous Vehicle Architecture

Figure 4:
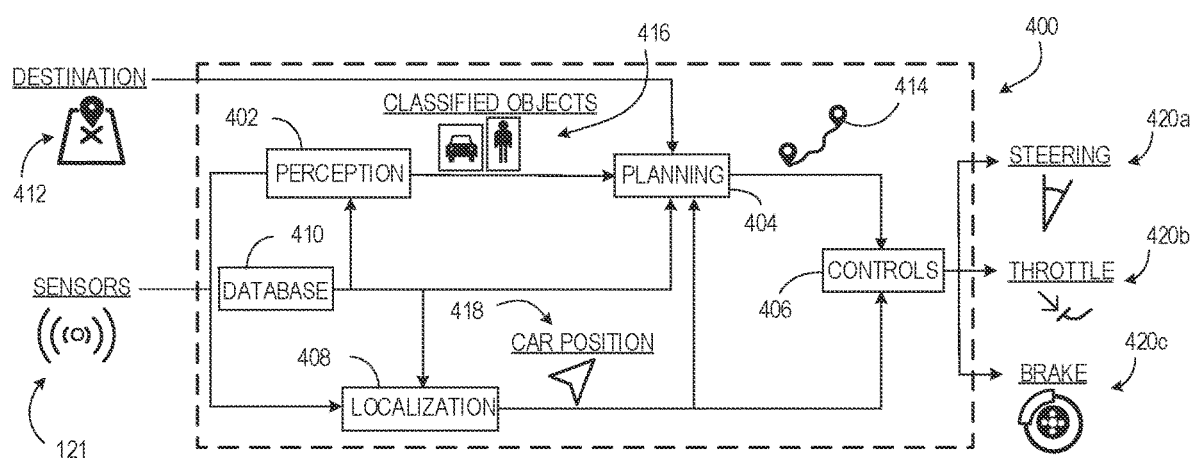
FIG. 4 shows an example architecture for an autonomous vehicle.

FIG. 4 shows an example architecture 400 for an autonomous vehicle (e.g., the AV 100 shown in FIG. 1). The architecture 400 includes a perception module 402 (sometimes referred to as a perception circuit), a planning module 404 (sometimes referred to as a planning circuit), a control module 406 (sometimes referred to as a control circuit), a localization module 408 (sometimes referred to as a localization circuit), and a database module 410 (sometimes referred to as a database circuit). Each module plays a role in the operation of the AV 100. Together, the modules 402, 404, 406, 408, and 410 may be part of the AV system 120 shown in FIG. 1. In some embodiments, any of the modules 402, 404, 406, 408, and 410 is a combination of computer software (e.g., executable code stored on a computer-readable medium) and computer hardware (e.g., one or more microprocessors, microcontrollers, application-specific integrated circuits [ASICs]), hardware memory devices, other types of integrated circuits, other types of computer hardware, or a combination of any or all of these things). Each of the modules 402, 404, 406, 408, and 410 is sometimes referred to as a processing circuit (e.g., computer hardware, computer software, or a combination of the two). A combination of any or all of the modules 402, 404, 406, 408, and 410 is also an example of a processing circuit.

In use, the planning module 404 receives data representing a destination 412 and determines data representing a trajectory 414 (sometimes referred to as a route) that can be traveled by the AV 100 to reach (e.g., arrive at) the destination 412. In order for the planning module 404 to determine the data representing the trajectory 414, the planning module 404 receives data from the perception module 402, the localization module 408, and the database module 410.

The perception module 402 identifies nearby physical objects using one or more sensors 121, e.g., as also shown in FIG. 1. The objects are classified (e.g., grouped into types such as pedestrian, bicycle, automobile, traffic sign, etc.) and a scene description including the classified objects 416 is provided to the planning module 404.

The planning module 404 also receives data representing the AV position 418 from the localization module 408. The localization module 408 determines the AV position by using data from the sensors 121 and data from the database module 410 (e.g., a geographic data) to calculate a position. For example, the localization module 408 uses data from a GNSS (Global Navigation Satellite System) sensor and geographic data to calculate a longitude and latitude of the AV. In an embodiment, data used by the localization module 408 includes high-precision maps of the roadway geometric properties, maps describing road network connectivity properties, maps describing roadway physical properties (such as traffic speed, traffic volume, the number of vehicular and cyclist traffic lanes, lane width, lane traffic directions, or lane marker types and locations, or combinations of them), and maps describing the spatial locations of road features such as crosswalks, traffic signs or other travel signals of various types. In an embodiment, the high-precision maps are constructed by adding data through automatic or manual annotation to low-precision maps.

The control module 406 receives the data representing the trajectory 414 and the data representing the AV position 418 and operates the control functions 420*a-c* (e.g., steering, throttling, braking, ignition) of the AV in a manner that will cause the AV 100 to travel the trajectory 414 to the destination 412. For example, if the trajectory 414 includes a left turn, the control module 406 will operate the control functions 420*a-c* in a manner such that the steering angle of the steering function will cause the AV 100 to turn left and the throttling and braking will cause the AV 100 to pause and wait for passing pedestrians or vehicles before the turn is made.

Autonomous Vehicle Inputs

Figure 5:
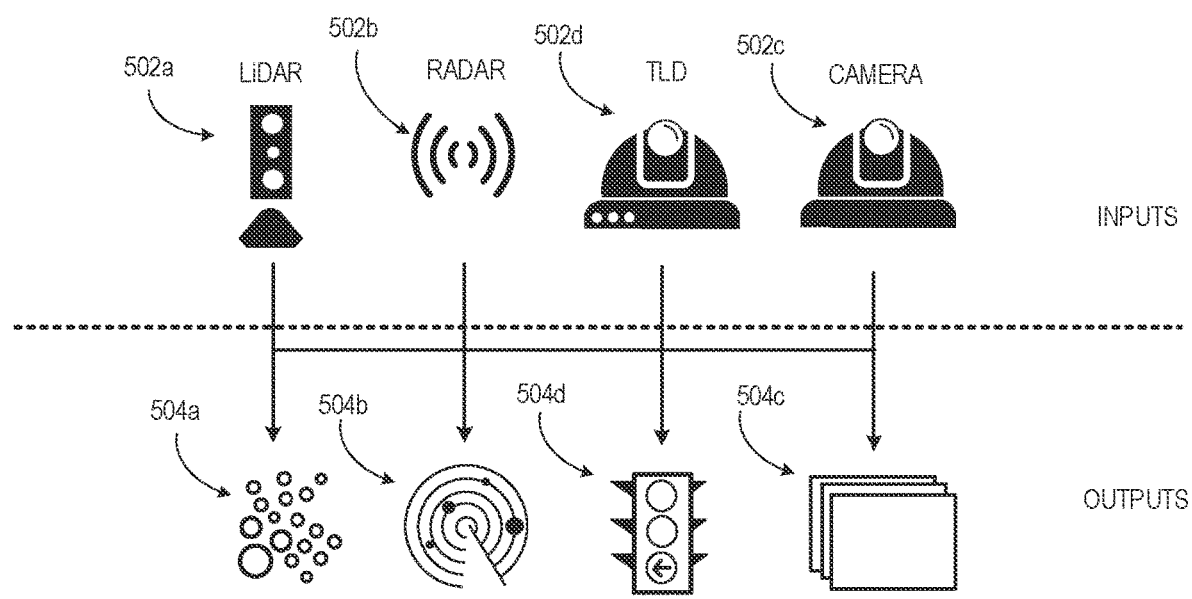
FIG. 5 shows an example of inputs and outputs that may be used by a perception module.

FIG. 5 shows an example of inputs 502*a-d* (e.g., sensors 121 shown in FIG. 1) and outputs 504*a-d* (e.g., sensor data) that is used by the perception module 402 (FIG. 4). One input 502*a* is a LiDAR (Light Detection and Ranging) system (e.g., LiDAR 123 shown in FIG. 1). LiDAR is a technology that uses light (e.g., bursts of light such as infrared light) to obtain data about physical objects in its line of sight. A LiDAR system produces LiDAR data as output 504*a*. For example, LiDAR data is collections of 3D or 2D points (also known as a point clouds) that are used to construct a representation of the environment 190.

Another input 502b is a RADAR system. RADAR is a technology that uses radio waves to obtain data about nearby physical objects. RADARs can obtain data about objects not within the line of sight of a LiDAR system. A RADAR system 502b produces RADAR data as output 504b. For example, RADAR data are one or more radio frequency electromagnetic signals that are used to construct a representation of the environment 190.

Another input 502c is a camera system. A camera system uses one or more cameras (e.g., digital cameras using a light sensor such as a charge-coupled device [CCD]) to obtain information about nearby physical objects. A camera system produces camera data as output 504c. Camera data often takes the form of image data (e.g., data in an image data format such as RAW, JPEG, PNG, etc.). In some examples, the camera system has multiple independent cameras, e.g., for the purpose of stereopsis (stereo vision), which enables the camera system to perceive depth. Although the objects perceived by the camera system are described here as "nearby," this is relative to the AV. In use, the camera system may be configured to "see" objects far, e.g., up to a kilometer or more ahead of the AV. Accordingly, the camera system may have features such as sensors and lenses that are optimized for perceiving objects that are far away.

Another input 502d is a traffic light detection (TLD) system. A TLD system uses one or more cameras to obtain information about traffic lights, street signs, and other physical objects that provide visual navigation information. A TLD system produces TLD data as output 504d. TLD data often takes the form of image data (e.g., data in an image data format such as RAW, JPEG, PNG, etc.). A TLD system differs from a system incorporating a camera in that a TLD system uses a camera with a wide field of view (e.g., using a wide-angle lens or a fish-eye lens) in order to obtain information about as many physical objects providing visual navigation information as possible, so that the AV 100 has access to all relevant navigation information provided by these objects. For example, the viewing angle of the TLD system may be about 120 degrees or more.

In some embodiments, outputs 504a-d are combined using a sensor fusion technique. Thus, either the individual outputs 504a-d are provided to other systems of the AV 100 (e.g., provided to a planning module 404 as shown in FIG. 4), or the combined output can be provided to the other systems, either in the form of a single combined output or multiple combined outputs of the same type (e.g., using the same combination technique or combining the same outputs or both) or different types type (e.g., using different respective combination techniques or combining different respective outputs or both). In some embodiments, an early fusion technique is used. An early fusion technique is characterized by combining outputs before one or more data processing steps are applied to the combined output. In some embodiments, a late fusion technique is used. A late fusion technique is characterized by combining outputs after one or more data processing steps are applied to the individual outputs.

Path Planning

Figure 6:
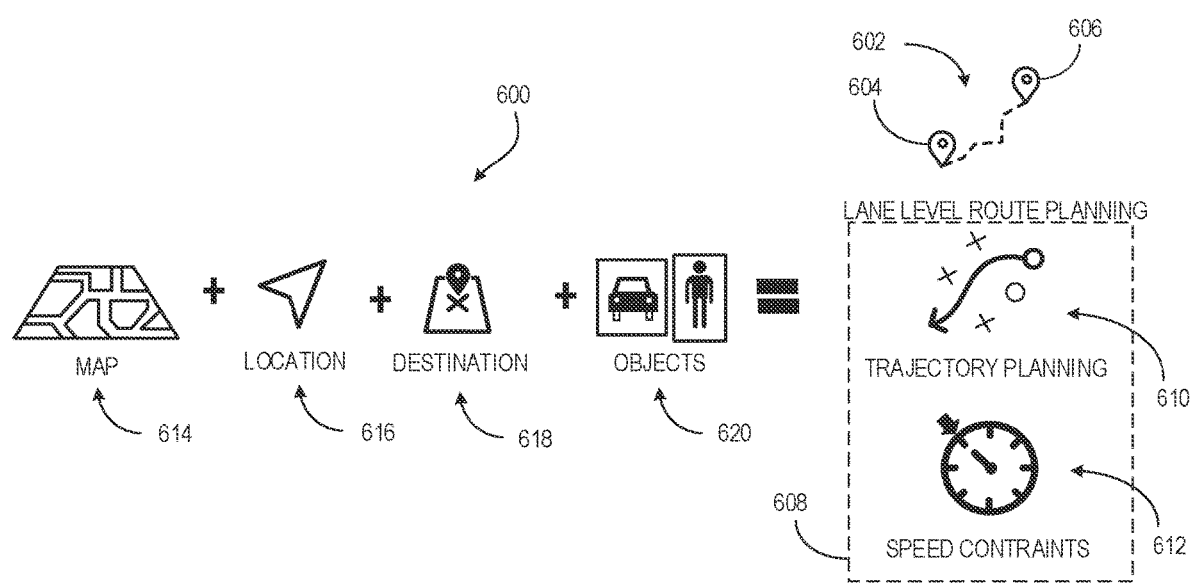
FIG. 6 shows a block diagram of the relationships between inputs and outputs of a planning module.

FIG. 6 shows a block diagram 600 of the relationships between inputs and outputs of a planning module 404 (e.g., as shown in FIG. 4). In general, the output of a planning module 404 is a route 602 from a start point 604 (e.g., source location or initial location), and an end point 606 (e.g., destination or final location). The route 602 is typically defined by one or more segments. For example, a segment is a distance to be traveled over at least a portion of a street, road, highway, driveway, or other physical area appropriate for automobile travel. In some examples, e.g., if the AV 100 is an off-road capable vehicle such as a four-wheel-drive (4WD) or all-wheel-drive (AWD) car, SUV, pick-up truck, or the like, the route 602 includes "off-road" segments such as unpaved paths or open fields.

In addition to the route 602, a planning module also outputs lane-level route planning data 608. The lane-level route planning data 608 is used to traverse segments of the route 602 based on conditions of the segment at a particular time. For example, if the route 602 includes a multi-lane highway, the lane-level route planning data 608 includes trajectory planning data 610 that the AV 100 can use to choose a lane among the multiple lanes, e.g., based on whether an exit is approaching, whether one or more of the lanes have other vehicles, or other factors that vary over the course of a few minutes or less. Similarly, in some implementations, the lane-level route planning data 608 includes speed constraints 612 specific to a segment of the route 602. For example, if the segment includes pedestrians or unexpected traffic, the speed constraints 612 may limit the AV 100 to a travel speed slower than an expected speed, e.g., a speed based on speed limit data for the segment.

In an embodiment, the inputs to the planning module 404 includes database data 614 (e.g., from the database module 410 shown in FIG. 4), current location data 616 (e.g., the AV position 418 shown in FIG. 4), destination data 618 (e.g., for the destination 412 shown in FIG. 4), and object data 620 (e.g., the classified objects 416 as perceived by the perception module 402 as shown in FIG. 4). In some embodiments, the database data 614 includes rules used in planning. Rules are specified using a formal language, e.g., using Boolean logic. In any given situation encountered by the AV 100, at least some of the rules will apply to the situation. A rule applies to a given situation if the rule has conditions that are met based on information available to the AV 100, e.g., information about the surrounding environment. Rules can have priority. For example, a rule that says, "if the road is a freeway, move to the leftmost lane" can have a lower priority than "if the exit is approaching within a mile, move to the rightmost lane."

Figure 7:
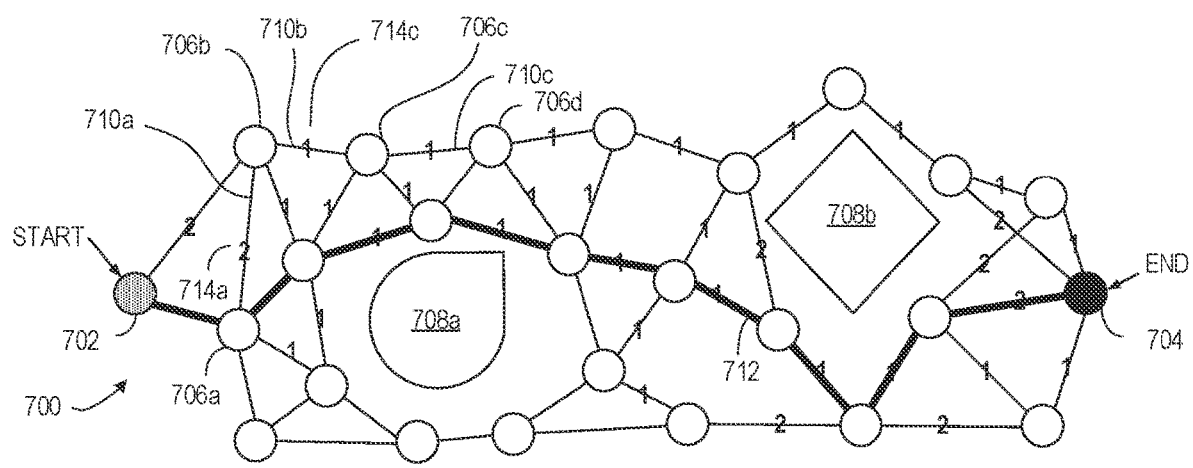
FIG. 7 shows a directed graph used in path planning.

FIG. 7 shows a directed graph 700 used in path planning, e.g., by the planning module 404 (FIG. 4). In general, a directed graph 700 like the one shown in FIG. 7 is used to determine a path between any start point 702 and end point 704. In real-world terms, the distance separating the start point 702 and end point 704 may be relatively large (e.g, in two different metropolitan areas) or may be relatively small (e.g., two intersections abutting a city block or two lanes of a multi-lane road).

In an embodiment, the directed graph 700 has nodes 706a-d representing different locations between the start point 702 and the end point 704 that could be occupied by an AV 100. In some examples, e.g., when the start point 702 and end point 704 represent different metropolitan areas, the nodes 706a-d represent segments of roads. In some examples, e.g., when the start point 702 and the end point 704 represent different locations on the same road, the nodes 706a-d represent different positions on that road. In this way, the directed graph 700 includes information at varying levels of granularity. In an embodiment, a directed graph having high granularity is also a subgraph of another directed graph having a larger scale. For example, a directed graph in which the start point 702 and the end point 704 are far away (e.g., many miles apart) has most of its information at a low granularity and is based on stored data, but also includes some high granularity information for the portion of the graph that represents physical locations in the field of view of the AV 100.

The nodes 706*a-d* are distinct from objects 708*a-b* which cannot overlap with a node. In an embodiment, when granularity is low, the objects 708*a-b* represent regions that cannot be traversed by automobile, e.g., areas that have no streets or roads. When granularity is high, the objects 708*a-b* represent physical objects in the field of view of the AV 100, e.g., other automobiles, pedestrians, or other entities with which the AV 100 cannot share physical space. In an embodiment, some or all of the objects 708*a-b* are a static objects (e.g., an object that does not change position such as a street lamp or utility pole) or dynamic objects (e.g., an object that is capable of changing position such as a pedestrian or other car).

The nodes 706*a-d* are connected by edges 710*a-c*. If two nodes 706*a-b* are connected by an edge 710*a*, it is possible for an AV 100 to travel between one node 706*a* and the other node 706*b*, e.g., without having to travel to an intermediate node before arriving at the other node 706*b*. (When we refer to an AV 100 traveling between nodes, we mean that the AV 100 travels between the two physical positions represented by the respective nodes.) The edges 710*a-c* are often bidirectional, in the sense that an AV 100 travels from a first node to a second node, or from the second node to the first node. In an embodiment, edges 710*a-c* are unidirectional, in the sense that an AV 100 can travel from a first node to a second node, however the AV 100 cannot travel from the second node to the first node. Edges 710*a-c* are unidirectional when they represent, for example, one-way streets, individual lanes of a street, road, or highway, or other features that can only be traversed in one direction due to legal or physical constraints.

In an embodiment, the planning module 404 uses the directed graph 700 to identify a path 712 made up of nodes and edges between the start point 702 and end point 704.

An edge 710*a-c* has an associated cost 714*a-b*. The cost 714*a-b* is a value that represents the resources that will be expended if the AV 100 chooses that edge. A typical resource is time. For example, if one edge 710*a* represents a physical distance that is twice that as another edge 710*b*, then the associated cost 714*a* of the first edge 710*a* may be twice the associated cost 714*b* of the second edge 710*b*. Other factors that affect time include expected traffic, number of intersections, speed limit, etc. Another typical resource is fuel economy. Two edges 710*a-b* may represent the same physical distance, but one edge 710*a* may require more fuel than another edge 710*b*, e.g., because of road conditions, expected weather, etc.

When the planning module 404 identifies a path 712 between the start point 702 and end point 704, the planning module 404 typically chooses a path optimized for cost, e.g., the path that has the least total cost when the individual costs of the edges are added together.

Autonomous Vehicle Control

Figure 8:
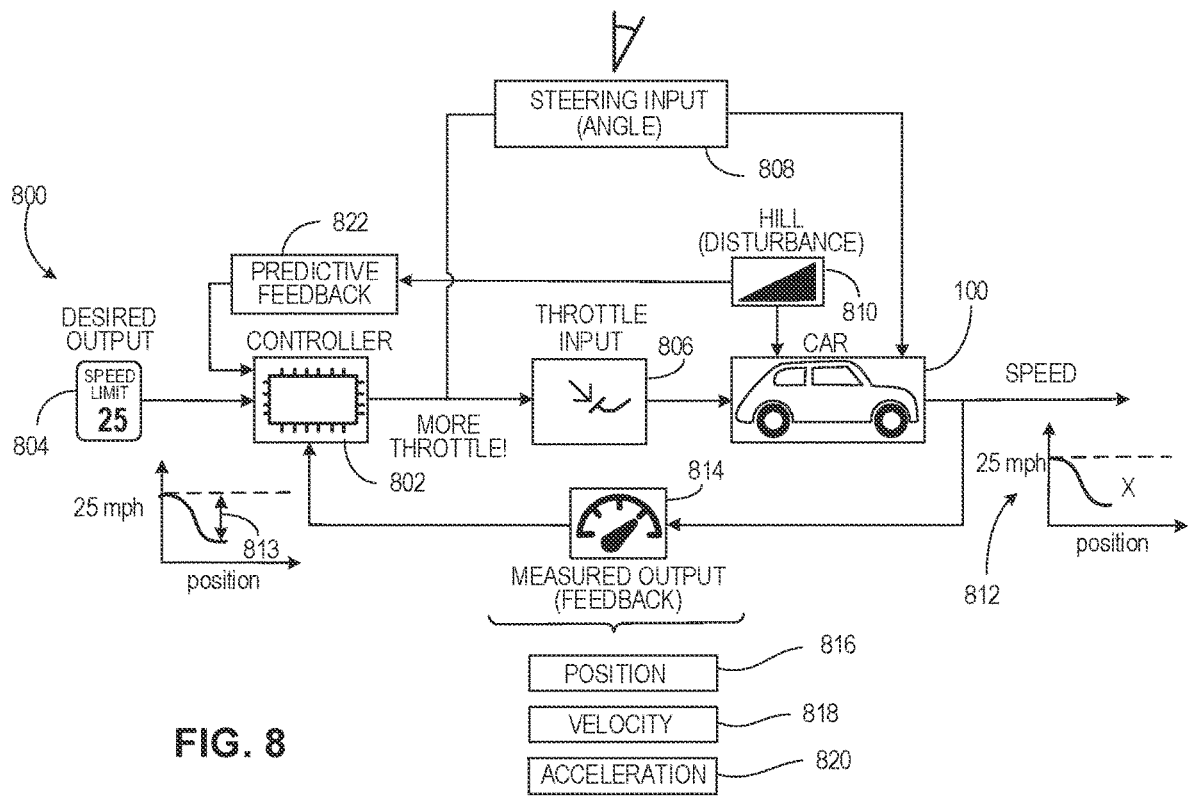
FIG. 8 shows a block diagram of the inputs and outputs of a control module.

FIG. 8 shows a block diagram 800 of the inputs and outputs of a control module 406 (e.g., as shown in FIG. 4). A control module operates in accordance with a controller 802 which includes, for example, one or more processors (e.g., one or more computer processors such as microprocessors or microcontrollers or both) similar to processor 304, short-term and/or long-term data storage (e.g., memory random-access memory or flash memory or both) similar to main memory 306, ROM 308, and storage device 310, and instructions stored in memory that carry out operations of the controller 802 when the instructions are executed (e.g., by the one or more processors).

In an embodiment, the controller 802 receives data representing a desired output 804. The desired output 804 typically includes a velocity, e.g., a speed and a heading. The desired output 804 can be based on, for example, data received from a planning module 404 (e.g., as shown in FIG. 4). In accordance with the desired output 804, the controller 802 produces data usable as a throttle input 806 and a steering input 808. The throttle input 806 represents the magnitude in which to engage the throttle (e.g., acceleration control) of an AV 100, e.g., by engaging the steering pedal, or engaging another throttle control, to achieve the desired output 804. In some examples, the throttle input 806 also includes data usable to engage the brake (e.g., deceleration control) of the AV 100. The steering input 808 represents a steering angle, e.g., the angle at which the steering control (e.g., steering wheel, steering angle actuator, or other functionality for controlling steering angle) of the AV should be positioned to achieve the desired output 804.

In an embodiment, the controller 802 receives feedback that is used in adjusting the inputs provided to the throttle and steering. For example, if the AV 100 encounters a disturbance 810, such as a hill, the measured speed 812 of the AV 100 is lowered below the desired output speed. In an embodiment, any measured output 814 is provided to the controller 802 so that the necessary adjustments are performed, e.g., based on the differential 813 between the measured speed and desired output. The measured output 814 includes measured position 816, measured velocity 818, (including speed and heading), measured acceleration 820, and other outputs measurable by sensors of the AV 100.

In an embodiment, information about the disturbance 810 is detected in advance, e.g., by a sensor such as a camera or LiDAR sensor, and provided to a predictive feedback module 822. The predictive feedback module 822 then provides information to the controller 802 that the controller 802 can use to adjust accordingly. For example, if the sensors of the AV 100 detect ("see") a hill, this information can be used by the controller 802 to prepare to engage the throttle at the appropriate time to avoid significant deceleration.

Figure 9:
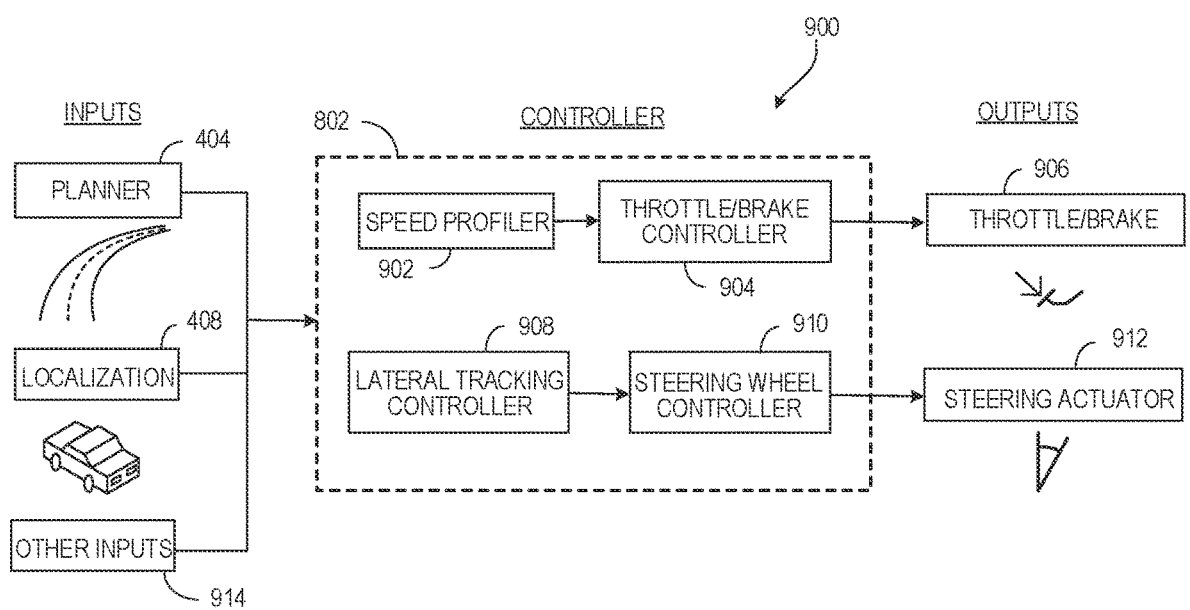
FIG. 9 shows a block diagram of the inputs, outputs, and components of a controller.

FIG. 9 shows a block diagram 900 of the inputs, outputs, and components of the controller 802. The controller 802 has a speed profiler 902 which affects the operation of a throttle/brake controller 904. For example, the speed profiler 902 instructs the throttle/brake controller 904 to engage acceleration or engage deceleration using the throttle/brake 906 depending on, e.g., feedback received by the controller 802 and processed by the speed profiler 902.

The controller 802 also has a lateral tracking controller 908 which affects the operation of a steering controller 910. For example, the lateral tracking controller 908 instructs the steering controller 910 to adjust the position of the steering angle actuator 912 depending on, e.g., feedback received by the controller 802 and processed by the lateral tracking controller 908.

The controller 802 receives several inputs used to determine how to control the throttle/brake 906 and steering angle actuator 912. A planning module 404 provides information used by the controller 802, for example, to choose a heading when the AV 100 begins operation and to determine which road segment to traverse when the AV 100 reaches an intersection. A localization module 408 provides information to the controller 802 describing the current location of the AV 100, for example, so that the controller 802 can determine if the AV 100 is at a location expected based on the manner in which the throttle/brake 906 and steering angle actuator 912 are being controlled. In an embodiment, the controller 802 receives information from other inputs 914, e.g., information received from databases, computer networks, etc.

Passenger Health Monitoring and Screening

Figure 10:
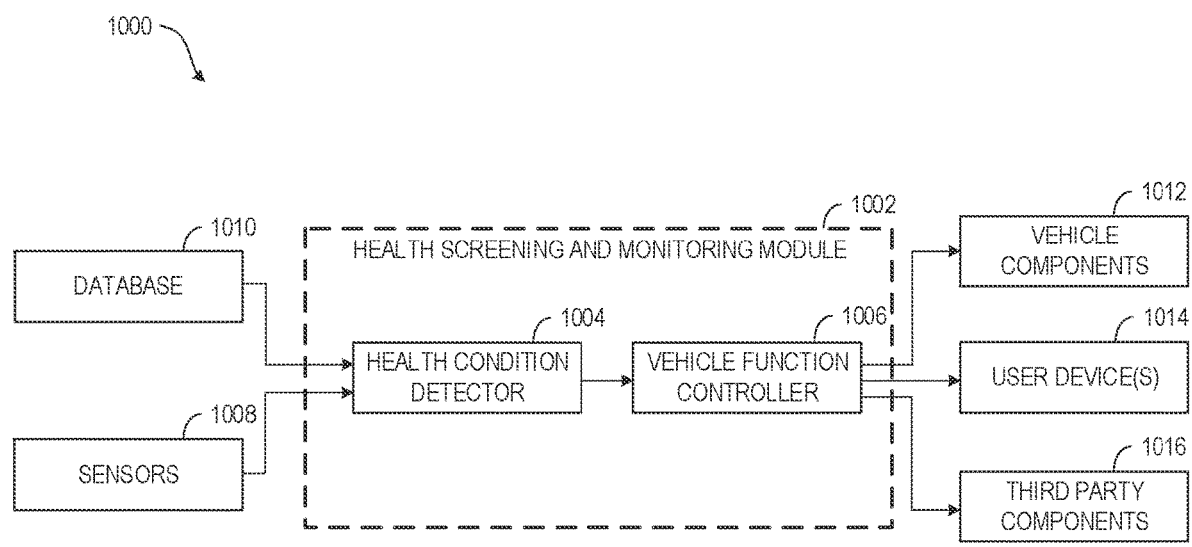
FIG. 10 shows a block diagram of the inputs, outputs, and components of a health screening and monitoring module.

FIG. 10 shows a block diagram 1000 of the inputs, outputs, and components of a health monitoring and screening module 1002. The health monitoring and screening module 1002 (sometimes referred to here as the "health module 1002") includes a health condition detector 1004 to detect a health condition of a user of a vehicle, and a vehicle function controller 1006 to execute vehicle functions in response to the detected health condition. Each of the health module 1002, health condition detector 1004, and the vehicle function controller 1006 can be part of a vehicle system (e.g., the AV system 120) and can be implemented by, for example, one or more processors (e.g., one or more computer processors such as microprocessors or microcontrollers or both) similar to processor 304, short-term and/or long-term data storage (e.g., memory random-access memory or flash memory or both) similar to main memory 306, ROM 308, and storage device 310, and instructions stored in memory that carry out operations of the respective component when the instructions are executed (e.g., by the one or more processors).

In general, the health condition detector 1004 processes data received from sensors 1008, databases 1010, and/or other data sources to detect one or more health conditions of a user of the vehicle (e.g., the AV 100). In some embodiments, the sensors 1008 include sensors disposed on or within the vehicle (e.g., sensors 121), sensors included in a user device (e.g., a smartphone, a wearable device, a tablet, etc.) in communication with the vehicle, or other sensors configured to generate sensor data related to the user as the user approaches or travels within the vehicle. In an embodiment, the databases 1010 include local and/or remote storage devices that store information regarding symptoms or other identifying features of health conditions. In an embodiment, the databases 1010 stores health information about a user of the vehicle, including historical health data detected by the vehicle or another vehicle, and the user can opt-in or otherwise accept disclosure of the health information to the health condition detector 1004 for the purpose of detecting health conditions.

The health condition detector 1004 is configured to detect a wide range of health conditions of a user, which may be updated over time. We use the term "health condition" broadly to refer to any actual or potential illness, injury, impairment, or physical or mental condition that affects or could affect the health of a person. The following description provides various examples of health conditions that can be detected by the health condition detector 1004. However, the following examples should not be construed as limiting, as the health condition detector 1004 can be configured to detect alternative or additional health conditions in some embodiments.

In an embodiment, the sensors 1008 include a temperature sensor, for example a temporal artery thermometer, or a forehead infrared scan thermometer, configured to produce data related to the body temperature of a user, e.g., as the user approaches or travels within the vehicle. The health condition detector 1004 compares the data received from the temperature sensor with an average or expected human body temperature received from, for example, the databases 1010. If the user exhibits an abnormal body temperature (e.g., a body temperature more than a threshold value above or below the average human body temperature), the health condition detector 1004 determines that the user has a health condition, such as a fever or hypothermia.

In an embodiment, the sensors 1008 include an audio sensor (e.g., a microphone) configured to produce audio data related to the user. The health condition detector 1004 processes the audio data to identify, for example, a cough or other audible symptom by the user. The health condition detector 1004 analyzes features of the cough or other audible symptom to diagnose the user with a particular health condition. In an embodiment, the health condition detector 1004 receives labeled audio data for coughs or other audible symptoms from the databases 1010 and applies pattern recognition or machine learning techniques to classify the cough or other audible symptom in the sensor data. The health condition detector 1004 then determines a likely health condition of the user based on the classification of the cough or other audible symptom. For example, the health condition detector 1004 employs a learning algorithm, such as a classification, regression, feature learning, or another supervised or unsupervised learning algorithm, to create a model, such as an artificial neural network, decision tree, support vector machine, or regression analysis, among others. The model is trained using training data (e.g., labeled audio data for coughs or other audible symptoms from the databases 1010) in order to make predictions or decisions regarding a likely health condition of the user based on the audio data received from the sensors 1008.

In an embodiment, the sensors 1008 include an image sensor (e.g., a camera or another optical sensor, such as a pupil dilation sensor) configured to produce image or video data related to the user. The health condition detector 1004 processes the image data to identify, for example, physical symptoms exhibited by the user. For example, using the image data, the health condition detector 1004 analyzes the motion of the user as the user approaches or travels within the vehicle to identify features of the user's motion, such as features of the user's gait, which may be indicative of a health condition. As another example, the health condition detector 1004 analyzes the image data using image classification techniques (e.g., machine learning techniques) to identify physical features of the user, such as sweat, blood, nasal discharge, pupil dilation, or facial droop, among other facial or physical features, that may be indicative of a health condition. As yet another example, the health condition detector 1004 analyzes the image data over time (e.g., as the user travels within the vehicle) using machine learning techniques to detect the onset of a motion-induced health condition, such as motion sickness.

In an embodiment, the health condition detector 1004 processes the image data to identify the presence of insects (e.g., fleas, lice, etc.) or animals within the vehicle or in an area proximate to the vehicle, or both. For example, the health condition detector 1004 analyzes the image data using image classification techniques to identify features in the image data indicative of the presence of insects or animals in the vehicle. In an embodiment, the health condition detector 1004 uses data from other sensors (e.g., allergen sensors) to detect the presence of insects or animals at the vehicle. Information about insects or animals at the vehicle can be used to inform the detection of a health condition for a user. For example, if the user begins sneezing or has another reaction to the presence of an insect or animal at the vehicle, it may be determined that the user is allergic to that insect or animal. As another example, if the user is known to have a particular allergy and is reacting to the presence of an insect or animal, it may be determined that the user's reaction is due to the allergy (rather than, for example, another ailment or condition). In an embodiment, if insects or animals are detected at the vehicle, the vehicle performs an action such as driving to a maintenance depot for cleaning, deactivating itself from the ride hailing network to stop taking on more passengers (or passengers who are allergic to the detected insect or animal), send warning messages to passengers inside the AV, or combinations of them, among others. Other actions that may be taken in response to detection animals or insects within the vehicle are described below with reference to the vehicle function controller 1006.

In an embodiment, the sensors 1008 include a pathogen sensor (e.g., a biosensor) configured to produce data regarding the presence of pathogens (e.g., airborne bacteria or viruses, body odor, etc.) within the vehicle or in an area proximate to the vehicle, or both. In some embodiments, pathogen sensor(s) are disposed within an air filtration or cooling system of the vehicle, within the cabin of the vehicle, or on an outside portion of the vehicle, or combinations of them, among others. The health condition detector 1004 processes the data received from the pathogen sensor along with pathogen data (e.g., pathogen genome data) received from the databases 1010 to determine a health condition of the user. For example, if a pathogen is detected at the vehicle after the user approaches or enters the vehicle, the health condition detector 1004 determines that the user has a health condition associated with the pathogen. In an embodiment, if the density of pathogens per unit volume of air being circulated inside the vehicle (e.g., the AV 100) exceeds a pre-determined threshold value, the vehicle performs an action such as driving to a maintenance depot for cleaning, deactivating itself from the ride hailing network to stop taking on more passengers, send warning messages to passengers inside the AV, or combinations of them, among others. In an embodiment, the action performed by the vehicle is selected from a set of possible actions based in part on the level (e.g., density) of pathogens within the vehicle. Other actions that may be taken in response to detection of a pathogen or a level of pathogens within the vehicle are described below with reference to the vehicle function controller 1006.

In an embodiment, the sensors 1008 include a mass or weight sensor (e.g., disposed in a seat of the vehicle) configured to produce data regarding the mass or weight of the user. The health condition detector 1004 compares the data received from the weight sensor with an average or expected weight for the user. The average or expected weight can account for the position of the user (e.g., seated) and sensed or known characteristics of the user (e.g., gender, age, height, etc.), and can be received from, for example, the databases 1010. In an embodiment, multiple weight sensors can be disposed at multiple locations in a seat of the vehicle to produce data regarding a weight distribution of the user. The health condition detector 1004 analyzes the weight distribution data received from the sensors along with reference data received from the databases 1010 to identify uneven or abnormal weight distributions of the user. In an embodiment, the health condition detector 1004 uses the weight or weight distribution data, or both, in combination with other sensor data to detect a health condition of the user.

In an embodiment, the sensors 1008 include a sensor (e.g., oximeter, electrocardiogram (EKG) sensor, electroencephalogram (EEG) sensor, etc.) configured to produce data regarding the heart rate, breathing pattern, or another vital sign of a user. In an embodiment, such sensors are disposed in a seat or seatbelt of the user. The health condition detector 1004 compares the data received from the sensors with an average or expected heart rate, breathing pattern, or other vital sign for the user. The average or expected values can account for sensed or known characteristics of the user (e.g., gender, age, height, etc.), and can be received from, for example, the databases 1010. The health condition detector 1004 uses the detected information on its own or in combination with other sensor data to detect a health condition of the user. For example, the health condition detector 1004 detects that a user is experiencing a heart attack if the user's heart rate is above or below a threshold value. As another example, the health condition detector 1004 detects that a user is experiencing an asthma attack if the user is known to have asthma and is exhibiting an abnormal breathing pattern.

After detecting one or more health conditions of the user, the health condition detector 1004 provides information indicative of the condition(s) to the vehicle function controller 1006. Based on the detected health condition(s), the vehicle function controller 1006 executes one or more vehicle functions. To do so, the vehicle function controller 1006 communicates or causes the vehicle system to communicate with vehicle components 1012, user devices 1014, or third party components 1016, or combinations of them, among others. The vehicle components 1012 include any hardware or software components that make up the vehicle (e.g., the AV 100) or the vehicle system (e.g., the AV system 120), such as the devices 101, modules 402, 404, 406, 408, and 410, etc. The user devices 1014 include devices (e.g., smartphones, wearable devices, tablets, etc.) associated with a user of the vehicle. The third party components 1016 include any hardware or software components other than the vehicle components 1012 or user devices 1014, such as other vehicles (e.g., vehicles 193), traffic lights, or emergency services providers, among others.

In general, the vehicle function controller 1006 is configured to execute vehicle functions based on the health condition of the user identified by the health condition detector 1004. For example, if the vehicle function controller 1006 receives information that the user is experiencing motion sickness, the controller 1006 communicates with the vehicle components 1012 to adjust driving parameters and provide a more comfortable ride for the user in order to alleviate the sickness. On the other hand, if the vehicle function controller 1006 receives information that the user is experiencing a stroke, the controller 1006 may respond by, for example, controlling components 1012 of the vehicle to transport the user to the nearest hospital for treatment.

In an embodiment, the vehicle function controller 1006 accounts for factors in addition to the health condition when determining an appropriate response. In some embodiments, the vehicle function controller 1006 accounts for factors such as characteristics of the user (e.g., age, gender, etc.), capabilities of the vehicle (e.g., whether the vehicle is capable of safely accommodating a sick user), features of the environment (e.g., weather, time of day, location, traffic, etc.), whether there are other users in the vehicle, whether the user has entered the vehicle, or whether the user has opted in to receiving care by the vehicle, or combinations of them, among others. Additional details on the factors considered by the vehicle function controller 1006 in determining an appropriate response to a health condition will become apparent from the following examples.

In an embodiment, the vehicle function controller 1006 alerts the user of a detected health condition. For example, the vehicle function controller 1006 sends an alert to the user's device 1014 (e.g., a SMS or MMS message, a notification in an application, etc.) or communicates with the vehicle components 1012 to display or provide an audible indication of the alert, or combinations of them. In an embodiment, the alert includes information regarding the detected health condition and a recommendation to the user, such as a recommendation to consult a medical professional to diagnose and treat the detected health condition. In an embodiment, the alert includes a list of nearby or user-preferred hospitals or other emergency services providers for treating the health condition. Selection of an emergency services provider can cause the vehicle to navigate to the selected emergency services provider, as described below.

In an embodiment, the vehicle function controller 1006 reroutes the vehicle in response to a detected health condition. For example, if the health condition indicates that the user is likely to vomit or otherwise needs to exit the vehicle, the vehicle function controller 1006 reroutes the vehicle to pull over at a safe stopping location. To do so, the vehicle function controller 1006 interacts with one or more vehicle components 1012, such as the planning module 404, the control module 404, or other components of the AV system 120, to identify, select, and navigate the vehicle to a safe stopping location.

As another example, if the health condition indicates a medical emergency (e.g., the user is showing signs of a stroke or heart attack), the vehicle function controller 1006 reroutes the vehicle to the nearest hospital or other emergency services provider. To do so, the vehicle function controller 1006 interacts with the vehicle components 1012 to update the destination and navigate the vehicle to the emergency services provider. In an embodiment, the vehicle function controller 1006 communicates with a third party 1016, such as an emergency services controller or another health authority, to be designated as an emergency vehicle. Such a designation includes, for example, permission to use emergency lanes and control traffic lights on route to the emergency services provider. If such a designation is granted, the vehicle function controller 1006 can control the vehicle components 1012 to navigate the vehicle in emergency lanes. The vehicle function controller 1006 can also cause the vehicle to communicate with traffic lights (e.g., though V2I communication, to enable traffic light preemption) and other third components 1016 such as other vehicles (e.g., through V2V communication, to alert them of the emergency situation) in order to reach the emergency services provider as quickly as possible. In an embodiment, the vehicle function controller 1006 shares information (e.g., sends an alert) about the detected health condition or other information about the user with the emergency services provider if the user consents to such a disclosure. In an embodiment, the vehicle function controller 1006 shares a location of the vehicle with the emergency services provider.

In an embodiment, the vehicle function controller 1006 adjusts a driving style of the vehicle in response to a detected health condition. For example, if it is determined (e.g., by the health condition detector 1004) that the user is experiencing motion sickness, the vehicle function controller 1006 adjusts the driving style of the vehicle to be slower, smoother, or otherwise more comfortable for the user to alleviate the sickness. On the other hand, the vehicle function controller 1006 may adjust the driving style of the vehicle to be faster or otherwise more aggressive in an emergency situation (e.g., when the vehicle is in route to an emergency services provider). To do so, the vehicle function controller 1006 communicates with the vehicle components 1012 to adjust one or more driving parameters of the vehicle to facilitate the desired driving style. Additional details on adjusting the driving style of the vehicle are described in U.S. patent application Ser. No. 16/656,655, titled "Systems and methods for controlling actuators based on load characteristics and passenger comfort," the entire contents of which is incorporated herein by reference.

In an embodiment, the vehicle function controller 1006 modifies an interior of the vehicle in response to a detected health condition. For example, if there are multiple users in the vehicle and it is determined that one or more of the users is experiencing a contagious health condition (e.g., a virus), the vehicle function controller 1006 engages a partition (e.g., an impermeable barrier) within the vehicle to separate the vehicle users and prevent spread of the contagion. As another example, the vehicle function controller 1006 reclines or otherwise adjusts a user's seat within the vehicle in response to an indication that the user is experiencing motion sickness or another health condition for which seat adjustment would be beneficial. In an embodiment, the vehicle (e.g., the AV 100) includes a modular interior, and the vehicle function controller 1006 rearranges the interior (e.g., by stowing, rotating, or otherwise moving seats or other components in the interior of the vehicle) in response to a health condition. For example, if the user is experiencing a health condition for which emergency services are required, the vehicle function controller 1006 rearranges the interior of the vehicle to mimic the interior of an ambulance to facilitate treatment of the user during travel to or upon arrival at an emergency services provider.

In an embodiment, the vehicle function controller 1006 adjusts a sound or smell within the vehicle in response to a detected health condition. For example, the vehicle function controller 1006 uses an audio output (e.g., speaker) in the vehicle to play a sound (e.g., a tone, a song, etc.) to mitigate a user's health condition, such as motion sickness. As another example, the vehicle function controller 1006 uses noise canceling or noise reduction techniques to block or cancel a sound within the vehicle to mitigate a user's health condition. As yet another example, the vehicle function controller 1006 uses a deodorizing agent, perfume, or other smell within the vehicle or adjusts an airflow within the vehicle as described below to reduce or eliminate a smell within the vehicle and mitigate a user's health condition.

In an embodiment, the vehicle function controller 1006 adjusts an airflow within the vehicle in response to a detected health condition. For example, if a user is experiencing motion sickness, a fever, a virus, or another health condition for which airflow would be beneficial (e.g., to alleviate the health condition or prevent spread of disease), the vehicle function controller 1006 increases airflow in the vehicle by opening the vehicle windows or engaging the vehicle air circulation system, which can include an air purifier. The vehicle function controller 1006 can also schedule adjustments to the airflow or air filtering (e.g., cycling of the air circulation, cooling, heating, or filtering systems).

In an embodiment, the vehicle function controller 1006 provides first aid to a user of the vehicle in response to a detected health condition. The type of first aid provided can depend on the detected health condition. For example, if it is determined that the user is vomiting or likely to vomit, the vehicle function controller 1006 provides (e.g., from a compartment within the vehicle) first aid in the form of a disposable vomit bag. As another example, if the user is experiencing a virus or other disease, the vehicle function controller 1006 dispenses first aid in the form of over-the-counter medicine which the user can take to alleviate symptoms, or a mask to prevent spread of the disease. As yet another example, if the user is experiencing a medical emergency for which more advanced first aid is required, the vehicle function controller 1006 engages one or more vehicle components 1012 to perform more advanced first aid such as administering cardiopulmonary resuscitation (CPR) or using an automated external defibrillator (AED).

In an embodiment, the vehicle function controller 1006 prevents a user from entering the vehicle in response to a detected health condition and optionally redirects the user to another vehicle. For example, if a user is determined to exhibit a contagious health condition before entering a vehicle having other passengers (such as in a ridesharing situation), the vehicle function controller 1006 prevents the user from entering and notifies the user of the situation (e.g., by sending an alert to the user's device 1014). In an embodiment, the vehicle function controller 1006 contacts another vehicle in the fleet (or a dispatcher of the fleet) to provide transport for the user that was denied entry to the vehicle. Alternatively, if the vehicle function controller 1006 determines that it is not advisable to refuse the user despite the risk to other passengers (e.g., because the health condition indicates an emergency, it is not safe for the user to wait at the pickup location, etc.), the vehicle function controller 1006 can accept the user and employ various safeguards to protect other users (e.g., engage touchless entry to and exit from the vehicle, provide a mask to the user, engage a partition, seating the user as far from other passengers in the vehicle as possible, increase airflow or air filtering in the vehicle, etc.).

In an embodiment, the vehicle function controller 1006 applies disinfectant (e.g., a disinfectant spray or foam, UV rays, etc.) within the vehicle after a user having a detected health condition exits the vehicle. For example, if a user is determined to have a contagious health condition, the vehicle function controller 1006 engages one or more vehicle components 1012 to disinfect and sterilize the interior of the vehicle (e.g., through spraying, fumigation, fogging, misting, shining UV rays, etc.). The vehicle can include materials that indicate (e.g., through changing colors) when the vehicle is disinfected and sterilized. In an embodiment, such as when the vehicle is used for ridesharing, the vehicle function controller 1006 adjusts (or causes a dispatcher to adjust) the routing for a subsequent trip such that the next trip includes few users or users who are at a low risk of infection due to the health condition detected for the previous user (e.g., based on the users' demographics).

Various modifications to the techniques describe here are possible. In an embodiment, a user self-reports a health condition (e.g., through a user device 1014, an audio interface, touch screen interface, or other interface in vehicle, etc.), and the vehicle function controller 1006 executes one or more vehicle functions based on the user-reported health condition. In an embodiment, the vehicle (e.g., the AV 100) is a roving diagnostic vehicle, and a user requests the vehicle to a location for diagnosis of health conditions (and subsequent transportation, if necessary).

In an embodiment, the health screening and monitoring module 1002 collects data for the user over multiple trips (with the user's consent) to provide a report of health conditions for the user over time and improve health condition detection. The data collected for the user can, with the user's consent, be aggregated with other health data for the user (e.g., collected by the user's device, such as a wearable device, or otherwise provided by the user), or aggregated with the user data from other consenting users. In an embodiment, the health screening and monitoring module 1002 uses the data aggregated for one or more users over multiple trips to perform analysis (e.g., statistical analysis) on a population of users. For example, the module 1002 analyzes the aggregated data to identify a percentage of users experiencing a particular health condition (e.g., a fever or cough), and compares the percentage with a historical measure to detect the onset of an illness (e.g., a seasonal illness, such as the flu). The module 1002 can use this information to, for example, tailor vehicle functions, such as cleaning and disinfecting policies for the vehicle (or fleet of vehicles) or inform public health agencies, among others.

In an embodiment, information regarding the health condition of a user (or group of users) is provided to third parties, such as advertisers or insurance companies. In an embodiment, the vehicle function controller 1006 sends information about the detected health condition or other information about the user to the third parties if the user consents to such a disclosure. The third parties can use the information about the detected health conditions to inform their interactions with the user. For example, if a third party is providing advertisements to the user (e.g., to the user's device, through a display or audio interface in the vehicle, etc.), it uses information about the detected health conditions for the user to provide appropriate or targeted advertisements to the user (e.g., advertisements about medication for treating a particular ailment experienced by the user).

Figure 11:
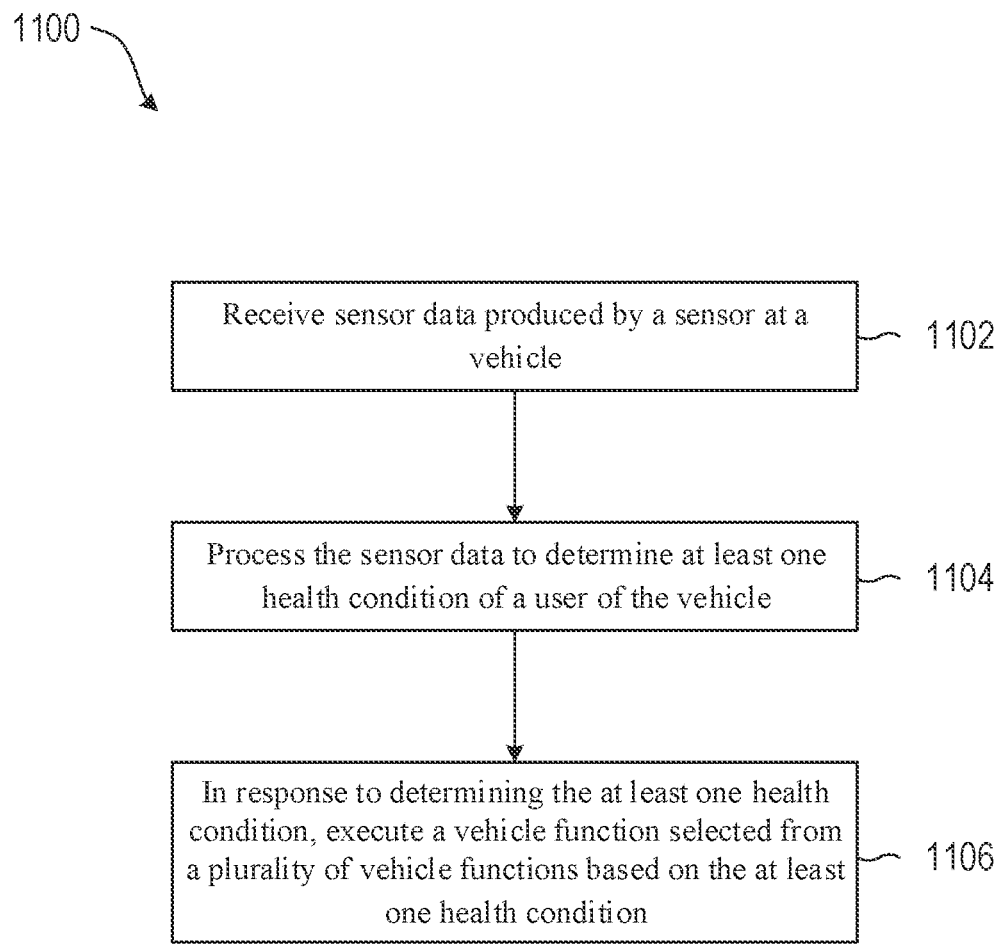
FIG. 11 shows a flowchart of an example process for screening and monitoring the health of a vehicle user.

FIG. 11 shows a flowchart of an example process 1100 for screening and monitoring the health of a vehicle user. In an embodiment, the vehicle is the AV 100 shown in FIG. 1, and the process 1100 is carried out by a processor, such as the processor 304 shown in FIG. 3.

The processor receives 1102 sensor data produced by a sensor at a vehicle. In an embodiment, the sensor is one of the sensors 1008 shown in FIG. 10 and includes an image sensor, audio sensor, temperature sensor, weight sensor, pathogen sensor, or another sensor configured to produce sensor data related to a user of the vehicle. In an embodiment, the sensor is configured to produce sensor data related to the user while the user is inside or proximate to the vehicle.

The processors processes 1104 the sensor data to determine at least one health condition of a user of the vehicle. In an embodiment, the sensor data is processed by executing stored instructions that carry out operations of the health condition detector 1004 shown in FIG. 10 when the instructions are executed by the processor (e.g., the processor 304).

In an embodiment, the sensor data is processed to identify data indicative of a cough by the user, and the data indicative of the cough is analyzed (e.g., by comparing with stored data characterizing coughs and corresponding ailment or querying a national database) to determine the at least one health condition of the user. In an embodiment, the sensor data is processed to identify data indicative of motion by the user (e.g., to detect gait before entry, to detect other motion within vehicle, etc.), and the data indicative of the motion is analyzed to determine the at least one health condition of the user. In an embodiment, the sensor data is processed to identify data indicative of a pathogen within the vehicle, and the data indicative of the pathogen is analyzed to determine the at least one health condition of the user. In an embodiment, the sensor data is processed to determine a body temperature of the user, and the at least one health condition of the user is determined based on the body temperature (e.g., by comparing the determined body temperate with an average or expected body temperature for the user). In an embodiment, the sensor data is processed to determine a facial feature of the user (e.g., pupil dilation, facial droop), and the at least one health condition of the user is determined based on the facial feature. In an embodiment, historical sensor data associated with the user is received, and the sensor data and the historical sensor data are processed to determine the at least one health condition of the user.

In response to determining the at least one health condition, the processor executes 1106 a vehicle function selected from multiple vehicle functions based on the at least one health condition. In an embodiment, the vehicle function is selected and executed by executing stored instructions that carry out operations of the vehicle function controller 1006 shown in FIG. 10 when the instructions are executed by the processor (e.g., the processor 304).

In an embodiment, the vehicle is configured to navigate from a starting location to a destination location along a trajectory, and executing the vehicle function includes altering at least one of the trajectory or the destination location of the vehicle. For example, the destination location is altered to an emergency services location. In an embodiment, executing the vehicle function includes altering a driving style of the vehicle (e.g., adopting a more comfortable or slower driving style to alleviate motion sickness, adopting a more aggressive or faster driving style to transport person to emergency services, etc.). In an embodiment, executing the vehicle function includes identifying a stopping location for the vehicle and navigating the vehicle to the stopping location. In an embodiment, executing the vehicle function includes adjusting an arrangement of a seat in the vehicle occupied by the user. In an embodiment, executing the vehicle function includes engaging a partition screen within the vehicle. In an embodiment, executing the vehicle function includes altering airflow within the vehicle.

In an embodiment, the vehicle includes a first aid component (e.g., a component for dispensing or administering medicine, applying CPR, etc.), and executing the vehicle function includes dispensing the first aid component to the user. In an embodiment, executing the vehicle function includes transmitting an alert to the user (e.g., to mobile device, displaying in vehicle, etc.), the alert including information indicative of the at least one health condition. In an embodiment, executing the vehicle function includes transmitting an alert to an emergency service, the alert including information indicative of at least one of a location of the vehicle or the at least one health condition of the user. In an embodiment, the vehicle includes a disinfectant component (e.g., UV rays, sterilizing mist/foam, etc.), and executing the vehicle function includes activating the disinfectant component within the vehicle. In an embodiment, executing the vehicle function includes transmitting a request to a health authority to allow the vehicle to operate in an emergency services mode to navigate to an emergency services provider. Operating in the emergency services mode can include using lanes designated for emergency vehicles or controlling traffic lights on a route to the emergency services provider In the foregoing description, embodiments of the invention have been described with reference to numerous specific details that may vary from implementation to implementation. The description and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising," in the foregoing description or following claims, what follows this phrase can be an additional step or entity, or a sub-step/sub-entity of a previously-recited step or entity.

What is claimed is:

1. A vehicle, comprising:
    at least one sensor configured to produce sensor data related to user of the vehicle;
    at least one computer-readable medium storing computer-executable instructions; and
    at least one processor communicatively coupled to the at least one sensor and the at least one computer-readable medium, the at least one processor configured to execute the computer executable instructions to perform operations comprising:
        receiving the sensor data produced by the at least one sensor during a first trip by a first user in the vehicle;
        processing the sensor data to determine at least one health condition of the first user during the first trip; and
        in response to determining the at least one health condition, executing at least one vehicle function based on the at least one health condition, wherein executing the at least one vehicle function comprises:
            causing selection of a second trip in the vehicle based on the at least one health condition of the first user during the first trip, wherein the second trip is subsequent to the first trip by the first user, and
            causing selection of one or more second users for the second trip in the vehicle based on the at least one health condition of the first user during the first trip, wherein the one or more second users comprise a user having below a threshold risk of infection due to the at least one health condition of the first user during the first trip.

2. The vehicle of claim 1, wherein causing selection of the second trip in the vehicle comprises causing selection of a number of the one or more second users for the second trip based on the at least one health condition of the first user during the first trip.

3. The vehicle of claim 2, wherein the number of one or more second users for the second trip is reduced based on the at least one health condition of the first user during the first trip.

4. The vehicle of claim 1, wherein causing selection of the second trip in the vehicle comprises causing selection of a type of the one or more second users for the second trip based on the at least one health condition of the first user during the first trip.

5. The vehicle of claim 1, wherein causing selection of the second trip in the vehicle comprises causing adjustment to the routing of the vehicle for the second trip.

6. The vehicle of claim 1, wherein executing the vehicle function comprises altering an interior of the vehicle.

7. A method, comprising:
    receiving sensor data produced by at least one sensor at a vehicle during a first trip by a first user in the vehicle;
    processing the sensor data to determine at least one health condition of the first user during the first trip; and
    in response to determining the at least one health condition, executing at least one vehicle function based on the at least one health condition, wherein executing the at least one vehicle fuction comprises:
        causing selection of a second trip in the vehicle based on the at least one health condition of the first user during the first trip, wherein the second trip is subsequent to the first trip by the first user, and causing selection of one or more second users for this second trip in the vehicle based on the at least one health condition of the first user during the first trip, wherein the one or more second users comprise a user having below a threshold risk of infection due to the at least one health condition of the first user during the first trip.

8. The method of claim 7, wherein causing selection of the second trip in the vehicle comprises causing selection of a number of the one or more second users for the second trip based on the at least one health condition of the first user during the first trip.

9. The method of claim 8, wherein the number of the one or more second users for the second trip is reduced based on the at least one health condition of the first user during the first trip.

10. The method of claim 7, wherein causing selection of the second trip in the vehicle comprises causing selection of a type of the one or more second users for the second trip based on the at least one health condition of the first user during the first trip.

11. The method of claim 7, wherein causing selection of the second trip in the vehicle comprises causing adjustment to the routing of the vehicle for the second trip.

12. The method of claim 7, wherein executing the vehicle function comprises altering an interior of the vehicle.

13. A non-transitory computer-readable storage medium comprising instructions executable by at least one processor to cause the at least one processor to:

receive sensor data produced by at least one sensor at a vehicle during a first trip by a first user in the vehicle;

process the sensor data to determine at least one health condition of the first user during the first trip; and in response to determining the at least one health condition, execute at least one vehicle function based on the at least one health condition, wherein executing the at least one vehicle function comprises:

causing selection of a second trip in the vehicle based on the at least one health condition of the first user during the first trip, wherein the second trip is subsequent to the first trip by the first user, and causing selection of one or more second users for this second trip in the vehicle based on the at least one health condition of the first user during the first trip, wherein the one or more second users comprise a user having below a threshold risk of infection due to the at least one health condition of the first user during the first trip.

14. The non-transitory computer-readable storage medium of claim 13, wherein causing selection of the second trip in the vehicle comprises causing selection of a number of the one or more second users for the second trip based on the at least one health condition of the first user during the first trip.

15. The non-transitory computer-readable storage medium of claim 14, wherein the number of the one or more users for the second trip is reduced based on the at least one health condition of the first user during the first trip.

16. The non-transitory computer-readable storage medium of claim 13, wherein causing selection of the second trip in the vehicle comprises causing selection of a type of the one or more second users for the second trip based on the at least one health condition of the first user during the first trip.

17. The non-transitory computer-readable storage medium of claim 13, wherein causing selection of the second trip in the vehicle comprises causing adjustment to the routing of the vehicle for the second trip.

\* \* \* \* \*

UNITED STATES PATENT AND TRADEMARK OFFICE
CERTIFICATE OF CORRECTION

| | | |
|---|---|---|
| PATENT NO. | : 11,919,539 B2 | Page 1 of 1 |
| APPLICATION NO. | : 17/937656 | |
| DATED | : March 5, 2024 | |
| INVENTOR(S) | : Eric Wolff, Abhimanyu Singh and Linh Pham | |

It is certified that error appears in the above-identified patent and that said Letters Patent is hereby corrected as shown below:

In the Claims

Claim 7, Column 26, Line 65, delete "fuction" and insert -- function --

Signed and Sealed this
Seventh Day of May, 2024

Katherine Kelly Vidal
*Director of the United States Patent and Trademark Office*